(12) United States Patent
Staib et al.

(10) Patent No.: US 10,892,040 B2
(45) Date of Patent: Jan. 12, 2021

(54) METHOD FOR EVALUATING A SET OF MEASUREMENT DATA FROM AN ORAL GLUCOSE TOLERANCE TEST

(71) Applicant: Roche Diabetes Care, Inc., Indianapolis, IN (US)

(72) Inventors: Arnulf Staib, Hepperheim (DE); Ortrud Quarder, Heidelberg (DE); Gerhard Werner, Weinheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 712 days.

(21) Appl. No.: 15/618,213

(22) Filed: Jun. 9, 2017

(65) Prior Publication Data

US 2017/0277865 A1    Sep. 28, 2017

Related U.S. Application Data

(63) Continuation of application No. 13/935,151, filed on Jul. 3, 2013, now abandoned, which is a continuation of application No. PCT/EP2011/006500, filed on Dec. 22, 2011.

(30) Foreign Application Priority Data

Jan. 7, 2011    (EP) .................................... 11000081

(51) Int. Cl.
*G01N 33/48*    (2006.01)
*G01N 33/50*    (2006.01)
*G16C 99/00*    (2019.01)
*G09B 23/28*    (2006.01)

(52) U.S. Cl.
CPC ............. *G16C 99/00* (2019.02); *G09B 23/28* (2013.01); *G01N 2800/00* (2013.01)

(58) Field of Classification Search
None
See application file for complete search history.

(56) References Cited

U.S. PATENT DOCUMENTS

| 7,766,829 | B2 | 8/2010 | Sloan et al. |
| 2003/0068666 | A1 | 4/2003 | Zweig |
| 2007/0083335 | A1 | 4/2007 | Moerman |
| 2007/0179771 | A1 | 8/2007 | Kouchi et al. |
| 2009/0145366 | A1* | 6/2009 | Inufusa ................. A01K 1/031 119/174 |
| 2011/0094896 | A1 | 4/2011 | Macfie et al. |

FOREIGN PATENT DOCUMENTS

EP    1 830 333 A1    9/2007

OTHER PUBLICATIONS

Corte, M. et al., "On a Mathematical Model for the Analysis of the Glucose Tolerance Curve," Diabetes, vol. 19, No. 6, 445-449 (Jun. 1970). 5 pages.
Crampin, E. J. et al., "Mathematical and computational techniques to deduce complex biochemical reaction mechanisms," Progress in Biophysics & Molecular Biology 86 (2004) 77-112. 36 pages.
Ghani, Muhammad A. et al., "The shape of plasma glucose concentration curve during OGTT predicts future risk of type 2 diabetes," Diabetes Metabolism Research and Reviews 2010; 26: 280-286. 7 pages.
Kroll, Martin H., "Biological variation of glucose and insulin includes a deterministic chaotic component," Biosystems 50 (1999), 189-201. 13 pages.
Lotz, Thomas et al., "A Minimal C-Peptide Sampling Method to Capture Peak and Total Prehepatic Insulin Secretion in Model-Based Experimental Insulin Sensitivity Studies," Journal of Diabetes Science and Technology, vol. 3, Issue 4, Jul. 2009, 875-886. 12 pages.
PCT/EP2011/006500—IPER dated Jul. 18, 2013.

* cited by examiner

*Primary Examiner* — Russell S Negin
(74) *Attorney, Agent, or Firm* — Woodard, Emhardt, Henry, Reeves & Wagner LLP

(57) ABSTRACT

A method is provided for evaluating a set of measurement data from an oral glucose tolerance test. The method may include calculating a similarity measure that quantifies the similarity between a time profile of the series of measured data of the glucose concentration and a corresponding glucose reference profile. The method may include calculating a further similarity measure that quantifies the similarity between the profile of the series of measured values of the further analyte concentration and the corresponding analyte sample profile, wherein the data set is represented by a point in a vector space that comprises coordinate axes that are formed by the similarity measures, whereby the coordinates of said point contain the calculated values of the similarity measures. The method also may include evaluating the position of the point with respect to reference points, which each represent a defined state of health, in order to calculate a parameter that specifies the state of the glucose metabolism of the patient.

22 Claims, 4 Drawing Sheets

METHOD FOR EVALUATING A SET OF MEASUREMENT DATA FROM AN ORAL GLUCOSE TOLERANCE TEST

CROSS-REFERENCE TO RELATED APPLICATIONS

The present U.S. utility application is a continuation of U.S. patent application Ser. No. 13/935,151 filed Jul. 3, 2013, which is related to and claims the priority benefit to patent cooperation treaty patent application serial no. PCT/EP2011/006500, filed Dec. 22, 2011, which claims priority to European patent application no. 1100081.7, filed Jan. 7, 2011. The contents of each of these applications are hereby incorporated by reference in their entirety into this disclosure.

TECHNICAL FIELD

The present specification generally relates to methods for evaluating a set of measurement data from an oral glucose tolerance test.

BACKGROUND

In an oral glucose tolerance test, an oral glucose solution is administered to a fasting patient and then the glucose concentration in the blood of the patient is measured at various time intervals. Usually, the profile of the blood sugar concentration is measured for a period of 2 hours. However, a glucose tolerance test can be carried out just as well for a shorter or longer period of time.

Determining the glucose concentration profile in response to the intake of glucose allows anomalies of glucose metabolism to be recognised. Oral glucose tolerance tests therefore allow impaired glucose utilisation to be detected and diabetes to be diagnosed.

SUMMARY

The present disclosure comprises methods for evaluating a set of measurement data from an oral glucose tolerance test.

In at least one embodiment of the present disclosure, a method for evaluating a set of measurement data from an oral glucose tolerance test is provided, whereby the set of measurement data includes a series of measurement data of the glucose concentration and, in addition, at least one series of measurement data of a further analyte concentration. In at least one embodiment, the method comprises calculating, by at least one computing device, a similarity measure that quantifies the similarity between a time profile of the series of measured data of the glucose concentration and a corresponding glucose reference profile, wherein the calculation of the similarity measure uses the series of measured data of the glucose concentration and one each of several predefined glucose reference profiles. Further, the method comprises calculating, by the at least one computing device, one value each of a further similarity measure that quantifies the similarity between the profile of the series of measured values of the further analyte concentration and the corresponding analyte sample profile, wherein the calculation of one value each of a further similarity measure uses the series of measured values of the further analyte concentration and one each of several predefined analyte reference profiles, wherein the data set is represented by a point in a vector space that comprises coordinate axes that are formed by the similarity measures, whereby the coordinates of said point contain the calculated values of the similarity measures. Additionally, the method comprises evaluating, by the least one computing device, the position of the point with respect to reference points, which each represent a defined state of health, in order to calculate a parameter that specifies the state of the glucose metabolism of the patient.

In at least one embodiment of the method, the method may comprise the step of evaluating, by the least one computing device, the position of the point characterizing the set of measurement data is evaluated with respect to the reference points by projecting the point onto a norm trajectory which follows a disease progression in said vector space from a healthy normal patient via a pre-diabetic conditions to a diabetic disease and contains at least a fraction of the reference points, wherein the length of a section of the trajectory from the start of the trajectory to the point of the trajectory onto which the point representing the set of measurement data was projected is used to determine the parameter specifying the state of glucose metabolism.

In at least one embodiment of the method, the vector space comprises multiple norm trajectories, each of which specify different disease progressions from a healthy normal patient via a pre-diabetic condition to an insulin-dependent diabetic disease, whereby the point characterizing the set of measurement data is projected onto the norm trajectory situated at the smallest distance from it.

In at least one embodiment of the method, the point characterizing the set of measurement data is, in addition, also projected onto a second norm trajectory situated at the second smallest distance from it.

In at least one embodiment of the method, the concentration profiles are normalized before calculating the similarity measures.

In at least one embodiment of the method, the similarity measures are calculated as scalar product of vectors, whereby one of the vectors is determined from the corresponding series of measured values and the other vector is determined from the corresponding sample profile.

In at least one embodiment of the method, the similarity measures are each calculated as scalar product of two normalized vectors.

In at least one embodiment of the method, a norm of a vector formed from the series of measured values of the glucose concentration is used as a further coordinate of the vector space.

In at least one embodiment of the method, a norm of a vector formed from the series of measured values of the further analyte concentration is used as further coordinate of the vector space.

In at least one embodiment of the method, at least one coordinate axis of the vector space specifies the value of a biometric or genetic variable that is measured independent of a concentration measurement.

In at least one embodiment of the method, the biometric variable is the body mass index, fraction of body fat, waist-to-hip ratio, blood pressure or heart rate.

In at least one embodiment of the method, the further analyte concentration is the concentration of a secretory hormone.

In at least one embodiment of the method, at least one coordinate axis of the vector space specifies the concentrations of a metabolite that shows no or little change on the time scale of an oral glucose tolerance test.

In at least one embodiment of the present disclosure, a non-transitory computer-readable medium is provided that comprises executable instructions such that when executed by at least one processor cause the at least one processor to: calculate a similarity measure that quantifies the similarity between a time profile of the series of measured values of the glucose concentration and a corresponding glucose reference profile, wherein the calculation of the similarity measure uses the series of measured values of the glucose concentration and one each of several predefined glucose reference profiles; calculate one value each of a further similarity measure that quantifies the similarity between the profile of the series of measured values of the further analyte concentration and the corresponding analyte sample profile, wherein the calculation of one value each of a further similarity measure uses the series of measured values of the further analyte concentration and one each of several predefined analyte reference profiles, wherein the data set is represented by a point in a vector space that comprises coordinate axes that are formed by the similarity measures, whereby the coordinates of said point contain the calculated values of the similarity measures; and evaluate the position of the point with respect to reference points, which each represent a defined state of health, in order to calculate a parameter that specifies the state of the glucose metabolism of the patient.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
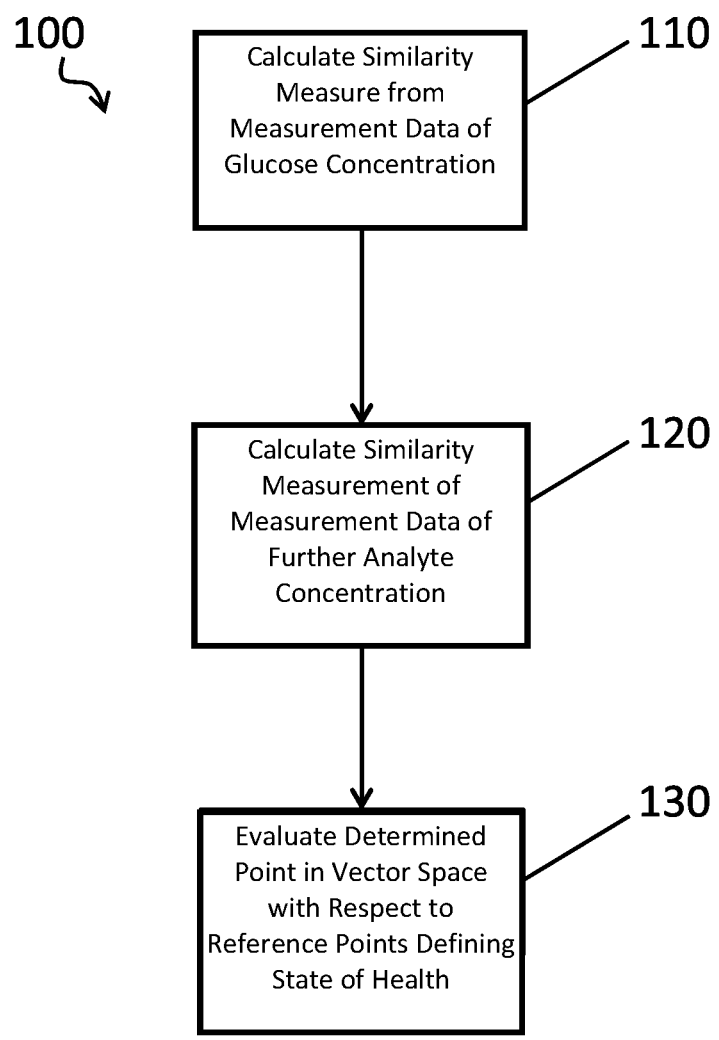
FIG. 1 shows a flowchart depicting the exemplary steps of at least one embodiment of the method of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Generally, the present disclosure provides methods for performing an evaluation of measurement data from oral glucose tolerance tests.

The efficacy of an oral glucose tolerance test can be improved by measuring the profile of further analytes in a body fluid of the patient, usually of blood and/or interstitial fluid in addition to the glucose concentration profile. Secretory hormones, such as insulin, pro-insulin, glucagon or C-peptide, are particularly well-suited. For this reason, a method according to the present disclosure evaluates a set of measurement data from an oral glucose tolerance test, where the set of measurement data includes a series of measurement data of the glucose concentration and, in addition, at least one series of measurement data of a further analyte concentration.

Turning to FIG. 1, a flowchart is depicted which shows the steps of an exemplary embodiment of a method 100 of the present disclosure. Initially, a similarity measure may be calculated from the series of measured values of the glucose concentration and one each of several predefined glucose reference profiles (exemplary calculating step 110). The similarity measure quantifies the similarity between the profile of the series of measured values of the glucose concentration and the corresponding glucose reference profile.

For example, the expected curve of the glucose concentration profile in a glucose tolerance test of a patient with a certain state of health can be used as glucose reference profile. Corresponding reference profiles can also be determined by means of testing sample patients who have already been diagnosed by other means, in particular for a fully healthy state of health (H-NG), a patient with type II diabetes (DT2), a normoglycaemic sample patient with metabolic syndrome (MS-NG), a sample patient with metabolic syndrome and impaired glucose tolerance (MS-IGT), a sample patient with metabolic syndrome and impaired fasting glucose (MS-IFG), and a sample patient, in whom the elevated fasting glucose is combined with impaired glucose tolerance (MS-CGI). The mathematic description of said profile curves is quite laborious and the evaluation therefore requires a major computational effort.

Exemplary glucose reference profiles may also be functions that are linear over time, or at least over sections thereof. Even simple functions of this type alone allow sections of the time profile of the glucose concentration to be characterized for a certain state of health. In particular, functions that are linear or linear over sections thereof and describe, only approximately, the increase or decrease of the glucose concentration during a part of the time period of a glucose tolerance test for a certain state of health can be used.

However, the similarity of the reference profiles to an actual profile is not obligatory, since, for example, it is also feasible to use a set of sufficiently different functions to approximate realistic time profiles, for example by linear combination, such as in the form of a Fourier series. A suitable set of functions can consist, for example, of polynomials, in particular polynomials of the type of $x^n$.

The series of measured values of the glucose concentration and a glucose reference profile may be used according to the present disclosure to calculate a value of a similarity measure. Basically, any calculation rule is suitable that yields a result describing the coincidence between the series of measurement data of the glucose concentration and the reference profile that is being considered.

For example, a correlation coefficient, in particular a Pearson product-moment correlation coefficient, can be used as a similarity measure. However, the similarity measure may also be calculated as the scalar product of two vectors, wherein one of the two vectors is determined from the corresponding series of measured values and the other vector is determined from the corresponding reference profile. For instance, the individual measured values, $g_1$, $g_2$, $g_3$ to $g_n$, which were determined for consecutive time points $t_1$, $t_2$ to $t_n$, can be used as components of a vector. In like manner, a vector can also be formed from a reference profile in that the concentration value of the reference profile at the relevant time point $t_1$, $t_2$ to $t_n$ is used as vector component.

In this context, normed concentration profiles, for example as scalar product of normed vectors, may be used to calculate the similarity measures. By this means, the mathematic effort can be simplified and the descriptive value of the similarity measure can be increased, since only the relative glucose concentration profile and thus the shape of the profile curve is being considered.

Turning back to FIG. 1, according to at least one embodiment of the present disclosure, the series of measured values of a further analyte concentration and each of several predefined analyte reference profiles may be used to calculate a value of a further similarity measure that quantifies the similarity between the profile of the series of measured values of the further analyte concentration and the corresponding analyte reference profile (exemplary calculating step 120). The profile curve of the analyte concentration of a patient with a certain state of health expected in a glucose tolerance test can be used as analyte reference profiles. In at least one exemplary embodiment, the analyte reference profiles use functions that are linear, at least over sections thereof.

In this context, the similarity measure with respect to the glucose concentration profile and the profile of the further analyte concentration are not necessarily calculated for the same and/or all available states of health, because significant differences in the profile of the analyte concentration between all states of health are not observed with all analytes. Pre-diabetic states of health and early stages of a diabetic disease can coincide over large parts of the analyte or glucose concentration profile such that it is feasible to forego the calculation of a similarity measure for the corresponding sections of the concentration profile and the corresponding states of health without lessening the significance of the robustness.

According to at least one embodiment of the present disclosure, the set of measured data from an oral glucose tolerance test and various reference profiles are first used to calculate a set of similarity measures, i.e. a set of variables which each are a measure of the similarity between the profile of the series of measured data and a reference profile.

In a further step of at least one exemplary method of the present disclosure, a vector space comprising coordinate axes that are formed by the similarity measures is considered. The data set of an individual with unknown state of health is characterized by a point in the vector space, whereby the coordinates of said point contain the calculated values of the similarity measures. Accordingly, if, for example, a first coordinate axis of the vector space is formed by the similarity measure of the time profile of the series of measured values of the glucose concentration and a first glucose reference profile, the value of that similarity measure is the first coordinate of the point representing the set of data.

In at least one exemplary method of the present disclosure, the position of this point may in at least one embodiment be evaluated with respect to reference points, which each represent a defined state of health (exemplary evaluating step 130). The reference points can be determined by glucose tolerance tests on subjects whose respective state of health is exactly known through an independent diagnosis. Reference points that can be used include, for example, the states of health of a fully healthy subject (H-NG), of a patient with insulin-dependent type II diabetes (DT2), of a normoglycemic sample patient with metabolic syndrome (MS-NG), of a sample patient with metabolic syndrome and impaired glucose tolerance (MS-IGT), of a sample patient with metabolic syndrome and impaired fasting glucose levels (MS-IFG), and of a sample patient, in whom the elevated fasting glucose is combined with impaired glucose tolerance (MS-CGI).

In order to minimize the influence of individual variations and particularities, a reference point may also be determined by averaging of oral glucose tolerance tests of multiple subjects with the same state of health.

In an instance where the state of health of the subject is unknown, the position of the point that represents the data set of a subject can be evaluated, for example, by calculating each distance to the various reference points. The unknown state of health can then be assigned to the reference point for which the smallest distance was determined. The magnitude of the distance can be a measure of the reliability of the assignment made. Accordingly, the distance can be used as a parameter that specifies the status of the glucose metabolism of the patient.

To evaluate the position of the point that represents the data set of an individual whose state of health is unknown, the point may be projected onto a norm trajectory that reflects a progression of disease in the vector space, from a healthy normal patient via one of the pre-diabetic conditions to a serious diabetic disease. A norm trajectory of this type contains at least a fraction of the above-mentioned reference points and can be determined from the measured data from oral glucose tolerance tests of a considerable number of subjects whose respective state of health is known from an independent diagnosis. Then, a point in the vector space can be calculated for each data set of a subject. Neglecting measuring errors and natural variation—said points are situated on a line that connects a data point of a healthy subject to the data point of a subject afflicted by serious diabetic disease. Points of subjects in various stages of disease are situated between the starting point and end-point of the trajectory.

The trajectory, although needed for evaluating the set of measured data from an oral glucose tolerance test of the present disclosure, does not need to be re-calculated for each new evaluation. Rather, it is sufficient to determine a norm trajectory of this type just once by evaluation of a large number of measured data of a multitude of subjects with different, and known, states of health with pre-defined reference profiles. Therefore, if the method according to the present disclosure is implemented using a computer program, the trajectory can be pre-defined. A user of the program then can operate without influencing the profile of the trajectory or its values.

Under ideal conditions, the point representing the set of measured data that is to be evaluated is situated on the norm trajectory. Due to inevitable measuring inaccuracies and natural variations, it must be expected in real-life that the point representing the set of measured data may be situated at a shorter or larger distance from the norm trajectory. In this case, the point of the norm trajectory that is closest to the point representing the set of measured data to be evaluated may be determined in a further step of the method.

Accordingly, the point of the norm trajectory may be determined through projecting the point representing the set of measured data onto the norm trajectory.

Said point of the norm trajectory subdivides the norm trajectory into two sections, namely a starting section from the start of the norm trajectory to said point, and an end-section from said point of the trajectory to the end of the trajectory.

The length ratios of these two sections of the trajectory contain the information regarding the distance of the state of health of the patient from a fully healthy status without diabetes and from a fully manifest serious diabetic disease. Accordingly, the length of a section of the trajectory from the start of the trajectory to the point of the trajectory onto which the point representing the data set was projected can therefore be used to determine a parameter that quantifies the extent of an impairment of glucose metabolism. This parameter can therefore specify the stage or risk of diabetic disease.

The parameter can, in at least one embodiment, be specified as the ratio of the length of the starting section of the trajectory and the overall length of the trajectory. In a fully healthy patient, the starting point of the norm trajectory is closest to the point representing the set of measured data to be evaluated such that the length of the starting section is equal to or close to zero. In a patient with fully manifest diabetic disease, though, the end of the trajectory is closest to the point representing the set of measured data to be evaluated, such that the length of the starting section of the trajectory divided by the overall length of the trajectory is equal, or close, to one.

It is significant in this context that multiple norm trajectories may exist in the considered vector space, whereby each specifies a different disease progression from a healthy normal patient via a pre-diabetic condition to an insulin-dependent diabetic disease. This is because diabetic disease may develop in a variety of ways and can be based on different causes or damage. For example, a diabetic disease can commence with the number of insulin-producing cells in the pancreas decreasing and the body's inherent insulin production coming to a standstill as a result. Alternatively, a diabetic disease may commence with muscle cells taking up glucose in progressively worse manner (insulin resistance) such that increased amounts of insulin or treatment with insulin sensitizers is required. Both the therapeutic options and the stages of disease on the way to the final stage of a diabetic disease are different in these two cases. Therefore, a separate trajectory can be considered in the vector space for each of these cases. Whereas the starting points and end-points of these trajectories coincide, their interim course differs.

If multiple norm trajectories are defined in the vector space, the point characterizing the data set is projected onto the norm trajectory situated at the shortest distance from it. In addition, the point characterizing the data set can also be projected onto a second norm trajectory situated at the second shortest distance from it. By this means, the second norm trajectory can be used as the basis for determination of a second parameter describing the status of glucose metabolism based on the length of a section of the trajectory from the start of the trajectory to the point of the trajectory onto which the point representing the data set was projected. Valuable information in this context can be obtained from the distance of the point representing the data set from the first norm trajectory and the distance from the second norm trajectory, e. g. from the relationship of the two distances. This is the case, because these distances indicate the reliability of the assignment to a norm trajectory that was made and thus the reliability of further disease progression to be expected. Cases, in which an unequivocal assignment to a norm trajectory cannot be made, may be a sign of multiple parallel damage mechanisms acting on the glucose metabolism, in particular in a pre-diabetic subject.

All coordinate axes of the vector space considered according to the invention can be provided by similarity measures. In this case, all coordinates of a point representing a data set from an oral glucose tolerance test can be specified as values of similarity measures. However, the vector space considered can just as well comprise one or more additional dimensions, i.e. have further coordinate axes for which coordinate values are calculated independent of the similarity measures. One further coordinate axis of the vector space can be formed, for example, by a norm of a vector formed from the series of measured values of the glucose concentration or analyte concentration. In this case, the point representing the data set in the vector space comprises the value of the corresponding norm as a further coordinate. The norm may be calculated in customary manner as Euclidian vector norm, i.e. as the root of the sum of squares of the individual vector components.

Just as well, biometric or genetic variables can be added as dimensions of the vector space. Examples of biometric variables include body mass index, fraction of body fat, and waist-to-hip ratio. Parameters such as blood pressure or heart rate can also be used as coordinates. Concentrations of metabolites showing no or little change on the time scale of an oral glucose tolerance test may also be used, such as cholesterol, cholesterol fractions (LDL and HDL), HbA1c or renal function parameters.

A method according to the present disclosure can be implemented efficiently through the use of a data processing device, i.e. a computer. Embodiments of the present disclosure therefore also relate to a computer program for implementing a method according to the present disclosure. A computer program product according to the present disclosure can be loaded into the memory of a computer and executes the steps of an embodiment of the method according to the present disclosure when the computer program product is run on a computer. The present disclosure also relates to a machine-readable storage medium on which a computer program product of this type is stored, i.e. a program that implements a method according to the invention when it is being run on a computer.

Figure 2:
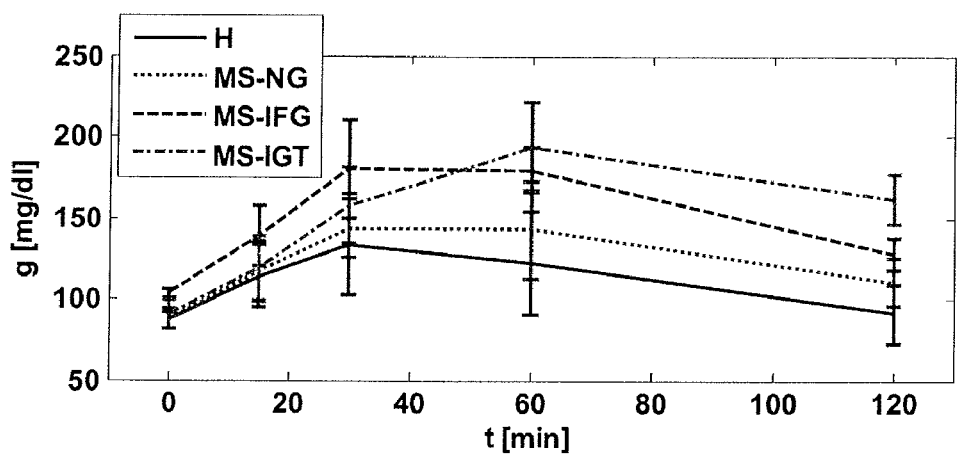
FIG. 2 shows an example of a glucose (g) concentration profile of an oral glucose tolerance test for different groups of patients.

FIG. 2 shows, for different patient groups, the mean profile of the glucose concentration (g) in units of mg per dl plotted versus time (t) during a glucose tolerance test for a period of 120 min. The individual patient groups are fully healthy people (H), normoglycaemic patients with metabolic syndrome (MS-NG), patients with metabolic syndrome and impaired glucose tolerance (MS-IGT), and patients with metabolic syndrome and impaired fasting glucose levels (MS-IFG). Moreover, the use of the method according to the present disclosure for other risk groups—risk of type II diabetes—, e.g. adipose people or individuals with a genetic predisposition, is also contemplated.

Figure 3:
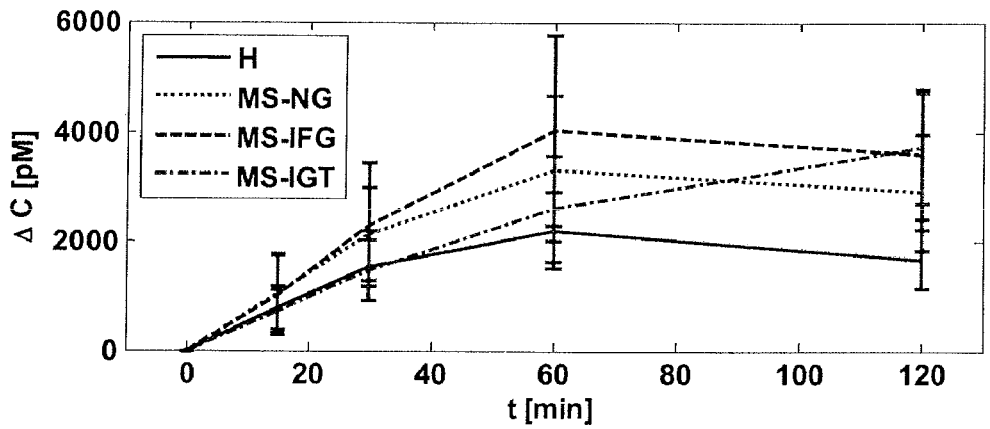
FIG. 3 shows an example of a C-peptide (C) concentration profile in an oral glucose tolerance test for different patient groups.

FIG. 3 shows the average profile of the C-peptide concentration during the oral glucose tolerance test for the patient groups of FIG. 2. In this context, rather than the absolute C-peptide concentration being plotted in FIG. 3, the change $\Delta C$ of said concentration with respect to a baseline value is plotted. In like manner, FIG. 4 shows the change of the proinsulin concentration $\Delta P$ with respect to a baseline value during the glucose tolerance test.

Figure 4:
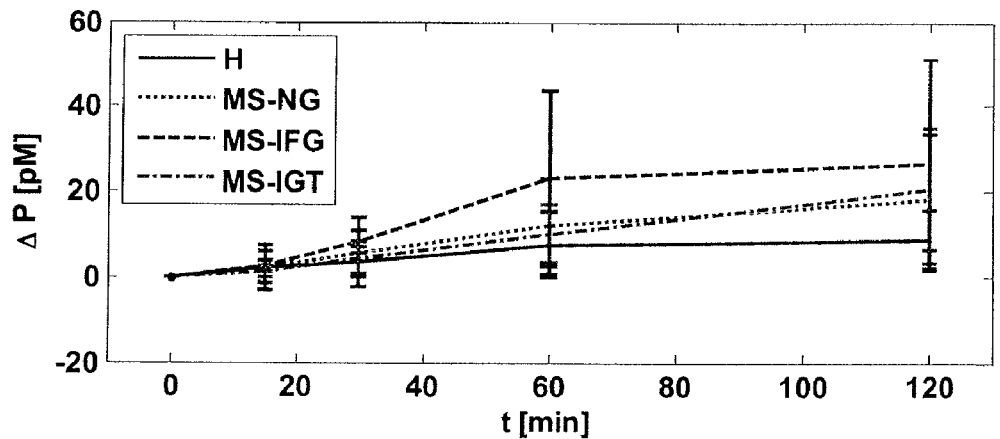
FIG. 4 shows an example of a proinsulin (P) profile in a glucose tolerance test for different patient groups.

In the example shown in FIGS. 2 to 4, analyte concentrations were measured in each case at the start of the glucose tolerance test (t=0), after 15 min, after 30 min, after 60 min, and after 120 min. Measured values of the glucose concentration are denoted $g_n$ hereinafter, whereby n indicates the time in minutes at which the concentration value was measured. In like manner, measured values of the C-peptide concentration, or to be more precise of the change with respect to a baseline value, are denoted $c_n$ and measured values of the proinsulin concentration, or to be more precise of the change with respect to a baseline value, are denoted $p_n$.

The measured values of an analyte concentration can be used to form a vector, in that each concentration value measured is used as a vector component. Accordingly, a vector $\underline{g}=(g_0, g_{15}, g_{30}, g_{60}, g_{120})$ can be formed from the measured values of the glucose concentration in the present case. In like manner, for example, the measured values of the C-peptide concentration and of the proinsulin concentration can be used to form vectors $\underline{c}$ and $\underline{p}$, respectively, which represent the respective series of measured values.

For the further evaluation, it is useful to normalize the vectors thus formed. A suitable norm is, in particular, the common quadratic definition, i.e. the Euclidian vector norm, $$\|\underline{g}\|=(\underline{g}\cdot\underline{g})^{1/2}$$

Reference profiles of the glucose concentration and of the further analyte concentrations are then defined for the further evaluation of the series of measured values and/or the vectors formed from them. Then vectors are formed for each of these sample profiles, which can represent a section of the expected time profile of the analyte concentration during an oral glucose tolerance test for a given state of health.

In the present illustrative embodiment, the following vectors are used as vectors for reference profiles, whereby M is the dimension of the vector space in each case:

The vector of the normalized body diagonal $\underline{N}_M=(1/\sqrt{M}, 1/\sqrt{M}, \ldots 1/\sqrt{M})$. Accordingly, if the vector includes five components, as is the case in a profile according to FIGS. 2 to 4, the resulting vector is $\underline{N}=(1, 1, 1, 1, 1)/\sqrt{5}$.

A vector $\underline{L}_M=(1, 2, 3, \ldots, M)/\|\underline{L}_M\|$, i.e. a linearly increasing sample profile. For the example of FIGS. 2 to 4, $\underline{L}=(1, 2, 3, 4, 5)/\sqrt{55}$.

A triangular (uneven M) or trapezoidal (even M) sample profile with the vector $\underline{D}_M=(1, 2, \ldots, M/2, M/2-1, \ldots, 1)/\|\underline{D}_M\|$, whereby M/2 is to be rounded up if M is uneven. For the case of FIGS. 2 to 4, $\underline{D}=(1, 2, 3, 2, 1)/\sqrt{19}$.

A similarity measure is calculated in a further step of the method and specifies the similarity of the concentration profile and the corresponding reference profile. The similarity measure can be calculated, for example, by calculating the scalar product of the respective vectors. In this context, the scalar product can, in turn, also be used as similarity measure or the angle formed by the two vectors can be calculated from the scalar product.

For example the following angles can be used as similarity measure of the glucose concentration profile:

$\alpha_g=\arccos(\underline{N}\cdot\underline{g})$, $\beta_g=\arccos(\underline{L}\cdot\underline{g})$, $\gamma_g=\arccos(\underline{D}\cdot\underline{g})$.

Accordingly, the following angles can be used as similarity measure for the profile of the C-peptide concentration and/or proinsulin concentration:

$\alpha_c=\arccos(\underline{N}\cdot\underline{c})$, $\beta_c=\arccos(\underline{L}\cdot\underline{c})$, $\gamma_c=\arccos(\underline{D}\cdot\underline{c})$ and/or $\alpha_p=\arccos(\underline{N}\cdot\underline{p})$, $\beta_p=\arccos(\underline{L}\cdot\underline{p})$, $\gamma_p=\arccos(\underline{D}\cdot\underline{p})$.

Each data set from an oral glucose tolerance test can be described by similarity measures of this type. A norm of the individual vectors representing the concentration profiles can be used just as well to supplement the characterisation of a set of measured data from a glucose tolerance test: for example, the Euclidian norm of the vectors, $\underline{g}$, $\underline{c}$, $\underline{p}$. One thus obtains for a set of measured data a set of variables, for example the variables, $\alpha_g$, $\beta_g$, $\gamma_g$, $\alpha_c$, $\beta_c$, $\gamma_c$, $\alpha_p$, $\beta_p$, $\gamma_p$, $\|\underline{g}\|$, $\|\underline{c}\|$, $\|\underline{g}\|$.

It is to be noted in this context that a larger or smaller number of reference profiles and, in particular, that other reference profiles can be used just as well. In particular, different reference profiles can be used for each individual analyte concentration. A set of measured data can therefore also be characterised through a different set of variables with a larger or smaller number of variables.

The values of the individual variables of the set of variables calculated from the measured data, for example the values of the variables $\alpha_g$, $\beta_g$, $\gamma_g$, $\alpha_c$, $\beta_c$, $\gamma_c$, $\alpha_p$, $\alpha_p$, $\gamma_p$, $\|\underline{g}\|$, $\|\underline{c}\|$, $\|\underline{g}\|$, can be used as coordinates in a vector space. By this means, each set of measured data from a glucose tolerance test can be represented by one point in a vector space. The coordinate axes of the vector space are then given by one of the variables each, whereby the value of said variable specifies the respective coordinate.

Figure 5:
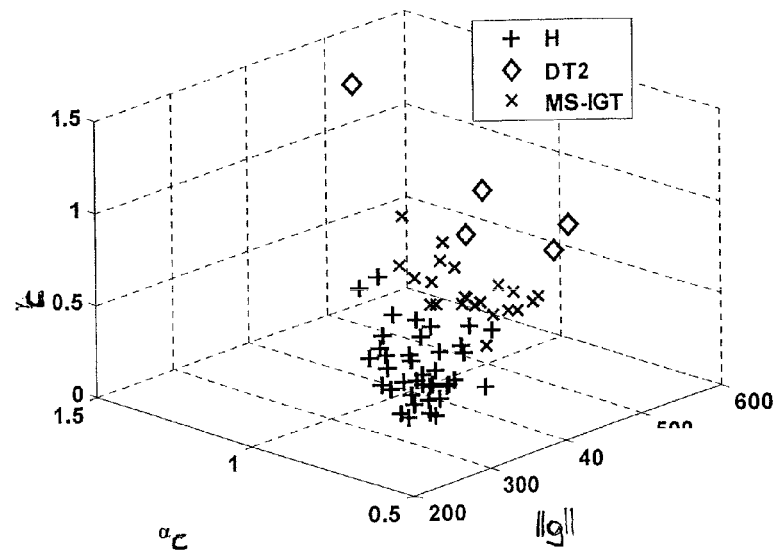
FIG. 5 shows data points representing the results of oral glucose tolerance tests for three different patient groups, in a three-dimensional vector space.
Figure 6:
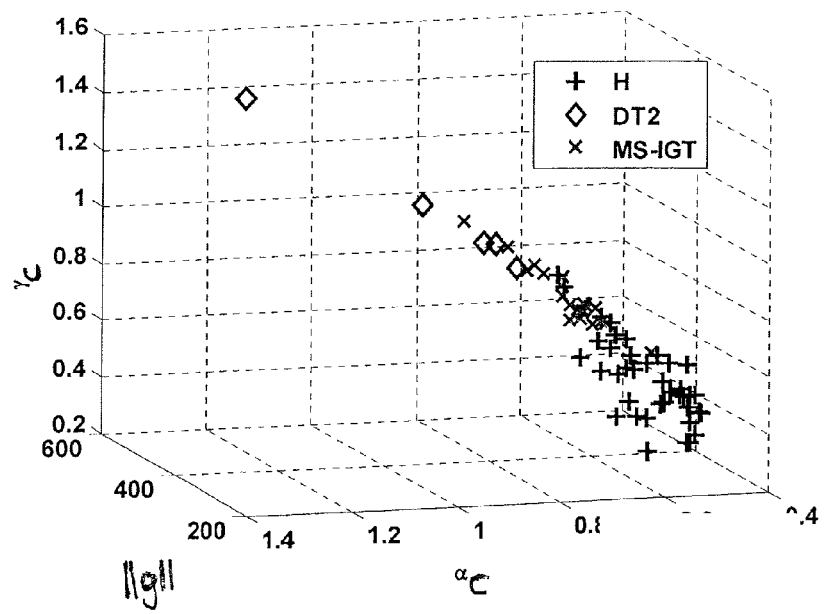
FIG. 6 shows another view related to FIG. 5.

FIGS. 5 and 6 show a schematic view in different viewing angles of a simplified example of a vector space of this type, in which points are marked, which each represent a set of measured data from an oral glucose tolerance test. Since only three dimensions can be shown graphically, the variables, $\|\underline{g}\|$, $\alpha_c$, and $\gamma_c$, were selected from the above-mentioned variables for FIGS. 5 and 6 for purposes of illustration. However, in a practical implementation of the method, a vector space of a higher dimension is used, i.e. a larger number of variables.

It is evident even from the simplified example of FIGS. 5 and 6 that the data points of various patient groups are clearly separated from each other in this vector space. Data points of healthy humans (H) are indicated by +, data points of patients with metabolic syndrome and impaired glucose tolerance (MS-IGT) are indicated by x, and data points of patients with type II diabetes (DT2) are indicated by ◊. The plot of FIG. 6 shows that the data points are situated approximately in the same plane and thus form a line in FIG. 6. Data points of patients with type II diabetes (DT2) are situated in the left upper part of said line. Data points of healthy samples (H) are situated in the right lower part. Accordingly, proceeding from right to left along the line, there are data points of type H first, then there are increasingly more data points of the MS-IGT-type, and lastly there are data points of the DT2-type. Accordingly, even in a simplified vector space, a line can be recognised that indicates how the data obtained from an oral glucose tolerance test change upon disease progression.

The use of values of the individual variables of the set of variables calculated from the measured data, i.e., for example, the values of the variables, $\alpha_g$, $\beta_g$, $\gamma_g$, $\alpha_c$, $\beta_c$, $\gamma_c$, $\alpha_p$, $\beta_p$, $\gamma_p$, $\|\underline{g}\|$, $\|\underline{c}\|$, $\|\underline{g}\|$, as coordinates in a vector space therefore defines a vector space, in which there is a trajectory that specifies a typical disease progression with increasing impairment of glucose metabolism. The trajectory therefore starts at a point that is expected for a fully healthy status and progresses via points representing pre-diabetic conditions or early diabetic disease, up to a point whose coordinates occur as values of variables in a patient with an insulin-dependent diabetic disease.

Said trajectory can be referred to as norm trajectory, since it describes the normal progression of disease. A norm trajectory can be obtained by evaluating the data of a considerable number of oral glucose tolerance tests of subjects whose state of health is known.

A point in said vector space is obtained from each set of measurement data by evaluating data from oral glucose tolerance tests for each stage of a diabetic disease. These points should coincide if the states of health are identical. However, it cannot be presumed that the state of health of two patients is exactly identical. Hence, some scattering of the points is to be expected. Despite this scattering, a norm trajectory can be calculated from a sufficiently large number of data points, for example by calculating the mean. Preferably, the mean of the values of a variable is calculated for data sets measured on patients with identical state of health, i.e. the center of gravity of a point cloud. However, it is feasible just as well to calculate a mean at an earlier stage of data analysis, for example a mean of the individual concentration profiles can be calculated in order to determine a typical profile of the concentration of glucose or other analyte for the respective state of health in a glucose tolerance test.

Figure 7:
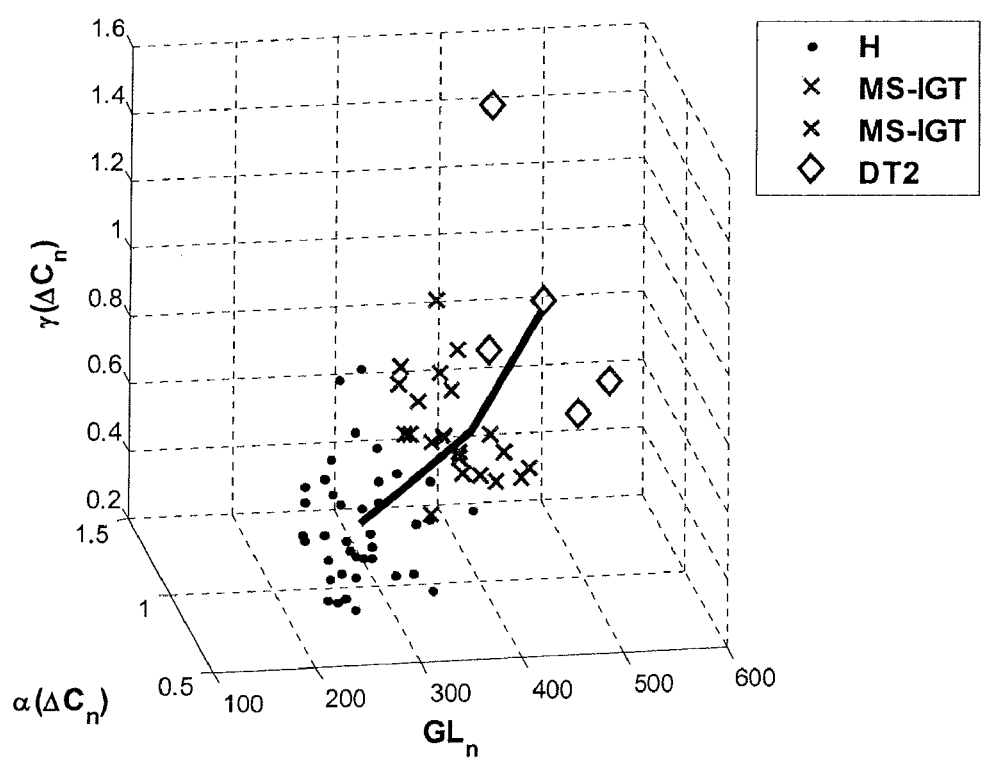
FIG. 7 shows an example of a norm trajectory with data points from oral glucose tolerance tests of different patient groups, according to at least one embodiment of the present disclosure.

FIG. 7 shows in exemplary manner a norm trajectory with data points from oral glucose tolerance tests of various patient groups, namely healthy patients H (•), patients with metabolic syndrome and impaired glucose tolerance (MS-IGT) (x) and insulin-dependent type II diabetics DT2 (◇).

In order to determine the state of health of the patient from a set of measurement data of an oral glucose tolerance test, it needs to be determined which point of the norm trajectory has the smallest distance from the point representing the set of measurement data from the glucose tolerance test. Thus, the point representing the measurement data from a glucose tolerance test is being projected onto the norm trajectory. The point of the norm trajectory thus determined subdivides the norm trajectory into two sections, namely a starting section and an end-section. The length of the section of the trajectory from the start of the trajectory to the point of the trajectory onto which the point representing the data set was projected is then used to determine a parameter that quantifies the extent of an impairment of glucose metabolism and thus indicates the disease stage of the patient. The parameter can, for example, be the ratio of the length of the starting section to the overall length of the trajectory.

The method also enables, in particular, a differentiation to be made within a given state of disease and/or health. Certain phases of disease can be seen with type II diabetes: treatment involving diet, treatment involving diet plus oral medication (e.g. metformin), treatment involving oral medication plus supplemental insulin, as well as fully insulin-dependent type II diabetes. This progression can be described in a vector space by a norm trajectory. The data point of a diabetic that has been tested can be assigned to a point of the norm trajectory and the disease stage can be recognized from its position on the norm trajectory. Further, embodiments of the method of the present disclosure allow a user to recognize when the time has come to switch from one treatment method to the next.

Systems and methods of the present disclosure for automatically displaying patterns in biological data may include one or more processors, and machine readable instructions. The machine readable instructions can cause the one or more processors to divide biological data into segments of interest. The one or more processors can transform, automatically, each of the segments of interest into a set of features according to a mathematical algorithm. Further, the one or more processors can cluster, automatically, the segments of interest into groups of clustered segments according to a clustering algorithm. The segments of interest can be grouped in the groups of clustered segments based at least in part upon the set of features. A cluster center can be associated with one of the groups of clustered segments. Moreover, the one or more processors can present, automatically, the cluster center on a human machine interface.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A method for treating a patient comprising:
 obtaining a set of measurement data from an oral glucose tolerance test administered to a patient, whereby the set of measurement data includes a series of measurement data of the glucose concentration;
 obtaining at least one series of measurement data of a further analyte concentration;
 calculating, by at least one computing device, a similarity measure that quantifies the similarity between a time profile of the measurement data of the glucose concentration and a corresponding glucose reference profile, wherein the calculation of the similarity measure uses the series of measurement data of the glucose concentration and one each of several predefined glucose reference profiles;
 calculating, by the at least one computing device, one value each of a further similarity measure that quantifies the similarity between the profile of the series of measurement data of the further analyte concentration and the corresponding further analyte sample profile, wherein the calculation of one value each of a further similarity measure uses the series of measurement data of the further analyte concentration and one each of several predefined further analyte reference profiles, wherein the data set of measurement data is represented by a point in a vector space that comprises coordinate axes that are formed by the similarity measures, whereby the coordinates of said point contain the calculated values of the similarity measures;
 evaluating, by the least one computing device, the position of the point with respect to reference points, which each represent a defined state of health, in order to calculate a parameter that specifies the state of the glucose metabolism of the patient;
 determining the disease stage of the patient;

determining a course of treatment for the patient from the determined disease stage; and treating the patient using the determined course of treatment.

2. The method of claim 1, wherein the step of evaluating, by the at least one computing device, the position of the point characterizing the set of measurement data is evaluated with respect to the reference points by projecting the point onto a norm trajectory which follows a disease progression in said vector space from a healthy normal patient via a pre-diabetic condition to a diabetic disease and contains at least a fraction of the reference points, wherein the length of a section of the trajectory from the start of the trajectory to the point of the trajectory onto which the point representing the set of measurement data was projected is used to determine the parameter specifying the state of glucose metabolism.

3. The method of claim 2, wherein the vector space comprises multiple norm trajectories, each of which specifies different disease progressions from a healthy normal patient via a pre-diabetic condition to an insulin-dependent diabetic disease, whereby the point characterizing the set of measurement data is projected onto the norm trajectory situated at the smallest distance from it.

4. The method of claim 3, wherein the point characterizing the set of measurement data is, in addition, also projected onto a second norm trajectory situated at the second smallest distance from it.

5. The method of claim 1, wherein the concentration profiles are normalized before calculating the similarity measures.

6. The method of claim 5, wherein the similarity measures are each calculated as a scalar product of two normalized vectors.

7. The method of claim 1, wherein the similarity measures are calculated as scalar products of vectors, whereby one of the vectors is determined from the corresponding series of measurement data and the other vector is determined from the corresponding sample profile.

8. The method of claim 1, wherein a norm of a vector formed from the series of measured values of the glucose concentration is used as a further coordinate of the vector space.

9. The method of claim 1, wherein a norm of a vector formed from the series of measured values of the further analyte concentration is used as a further coordinate of the vector space.

10. The method of claim 1, wherein at least one coordinate axis of the vector space specifies the value of a biometric or genetic variable that is measured independent of a concentration measurement.

11. The method of claim 10, wherein the biometric variable is selected from the group consisting of the body mass index, fraction of body fat, waist-to-hip ratio, blood pressure and heart rate.

12. The method of claim 1, wherein the further analyte concentration is the concentration of a secretory hormone.

13. The method of claim 1, wherein at least one coordinate axis of the vector space specifies the concentrations of a metabolite that shows no or little change on the time scale of an oral glucose tolerance test.

14. The method of claim 1 in which the course of treatment selected from the group consisting of diet, diet plus oral medication, oral medication plus supplemental insulin, and treatment as fully insulin-dependent type II diabetes.

15. The method of claim 14 and which further includes determining a course of treatment involving diet.

16. The method of claim 14 and which further includes determining a course of treatment involving diet plus oral medication.

17. The method of claim 14 and which further includes determining a course of treatment involving oral medication plus supplemental insulin.

18. The method of claim 14 and which further includes determining a course of treatment involving treatment as fully insulin-dependent type II diabetes.

19. The method of claim 1 and which further includes switching the patient from one course of treatment to another course of treatment for the diabetic condition.

20. The method of claim 19 in which said switching involves switching between two different courses of treatment selected from the group consisting of diet, diet plus oral medication, oral medication plus supplemental insulin, and treatment as fully insulin-dependent type II diabetes.

21. The method of claim 1 in which said evaluating further comprises specifying a health condition for the patient selected from the group consisting of full healthy state of health, type II diabetes, normoglycaemic with metabolic syndrome, metabolic syndrome and impaired glucose tolerance, metabolic syndrome and impaired fasting glucose, and elevated fasting glucose combined with impaired glucose tolerance.

22. A method for determining a course of treatment for a specified state of glucose metabolism comprising:

administering an oral glucose tolerance test and obtaining a set of measurement data including a first series of measurement data of the glucose concentration;

using the first series of measurement data to determine a time profile of the glucose measurement data;

selecting a corresponding glucose reference profile from a selection of several predefined glucose reference profiles obtaining a second series of measurement data of analyte concentration of a secretory hormone selected from the group consisting of insulin, pro-insulin, glucagon and C-peptide;

using the second series of measurement data to determine a profile of the analyte measurement data;

selecting a corresponding analyte reference profile from a selection of several predefined analyte reference profiles;

using both the selected glucose reference profile and the selected analyte reference profile to identify a specified state of glucose metabolism;

determining a course of treatment for the specified state of glucose metabolism, the course of treatment being selected from the group consisting of diet, diet plus oral medication, oral medication plus supplemental insulin, and treatment as fully insulin-dependent type II diabetes; and treating the patient using the determined course of treatment.

* * * * *